(12) United States Patent
Thoren et al.

(10) Patent No.: US 9,078,710 B2
(45) Date of Patent: Jul. 14, 2015

(54) ORTHOPEDIC COMPRESSION/DISTRACTION DEVICE

(71) Applicant: Wright Medical Technology, Inc., Arlington, TN (US)

(72) Inventors: Brian Thoren, Memphis, TN (US); Daniel McCormick, Bartlett, TN (US); David Harness, Eads, TN (US); Wesley Reed, Libertyville, IL (US); Thomas Cramer, Gainesville, FL (US); Gary Lowery, Eads, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 170 days.

(21) Appl. No.: 13/712,300

(22) Filed: Dec. 12, 2012

(65) Prior Publication Data
US 2014/0163575 A1    Jun. 12, 2014

(51) Int. Cl.
*A61B 17/88* (2006.01)
*A61B 17/70* (2006.01)

(52) U.S. Cl.
CPC .................................. *A61B 17/7077* (2013.01)

(58) Field of Classification Search
CPC ... A61B 17/88; A61B 17/885; A61B 17/7077
USPC ................ 606/60, 69, 101, 104, 246–279, 10
See application file for complete search history.

(56) References Cited

U.S. PATENT DOCUMENTS

| | | | |
|---|---|---|---|
| 6,245,071 B1 | 6/2001 | Pierson | |
| 6,793,655 B2 | 9/2004 | Orsak | |
| 7,011,658 B2 | 3/2006 | Young | |
| 8,568,417 B2 | 10/2013 | Petrzelka | |
| 2006/0004380 A1 | 1/2006 | DiDomenico et al. | |
| 2006/0235389 A1* | 10/2006 | Albert et al. | 606/61 |
| 2006/0247645 A1* | 11/2006 | Wilcox et al. | 606/86 |
| 2006/0247649 A1 | 11/2006 | Rezach et al. | |
| 2009/0204115 A1* | 8/2009 | Dees et al. | 606/62 |
| 2011/0077690 A1* | 3/2011 | Shin et al. | 606/278 |
| 2011/0245876 A1* | 10/2011 | Brumfield | 606/264 |
| 2012/0029566 A1* | 2/2012 | Rezach | 606/264 |

FOREIGN PATENT DOCUMENTS

KR    10-0391252    7/2003

OTHER PUBLICATIONS

DMCD K-Wire Distractor and Compressor 5 stop, http://friedrich-daniels.com/content/dmcd-k-wire-distractor-and-compressor-5-stop, Apr. 17, 2013, 2 pages.
International Search Report and Written Opinion issued on Aug. 14, 2014 for corresponding PCT Application No. PCT/US2014/028641.
Search Report issued on Dec. 9, 2014 in corresponding PCT Application No. PCT/US2014/028765.

* cited by examiner

*Primary Examiner* — Christopher Beccia
(74) *Attorney, Agent, or Firm* — Duane Morris LLP

(57) ABSTRACT

An orthopedic device for compressing or distracting bone parts includes an elongated body with two arms extending transversely away from the body. One arm is a stationary arm affixed to one end of the body and a second arm is a longitudinally movable. The two arms extend from the elongated body in the same direction and parallel to each other. The orthopedic device also includes a locking sleeve hingeably connected to the outer end of each of the first and second arms by a hinge joint, where each locking sleeve is configured for lockably receiving an elongated pin using a collet and a captured collet nut.

19 Claims, 5 Drawing Sheets

ORTHOPEDIC COMPRESSION/DISTRACTION DEVICE

CROSS-REFERENCE TO RELATED APPLICATION

None.

FIELD OF THE INVENTION

The present disclosure relates to an orthopedic device that can be used for compression or distraction of bone parts.

BACKGROUND

Orthopedic devices utilizing elongated pins as fasteners for compression or distraction of bone parts finds many uses for treating orthopedic patients. "Elongated pins" will be used herein to refer to various pins and wires, such as K-wires, used for fixating bone parts or providing anchors. Therefore, there is a continuing need for an improved orthopedic device that expands the scope and ability of the orthopedic surgeons in treating patients in a variety of conditions.

SUMMARY

According to an aspect of the present disclosure an orthopedic device that can be used for compression or distraction of bone parts is described. The orthopedic device comprises an elongated body having first and second ends, a first arm member attached to and transversely extending away from said first end and terminating at an outer end and a second arm member transversely extending away from said elongated body and having a base portion and an outer end. The base portion is configured and adapted to movably engage the elongated body allowing the second arm member to be longitudinally movable along said elongated body. Said second arm member extends from the elongated body in the same direction as the first arm member. The orthopedic device also includes a locking sleeve hingeably connected to the outer end of each of the first and second arm members by a hinge joint, wherein said each locking sleeve is configured for lockably receiving an elongated pin. The locking sleeve comprises an elongated shaft having an elongated pin receiving bore extending therethrough and a collet provided at one end of the elongated shaft. The collet comprises a plurality of collet arms provided with screw threads integrally formed on their exterior surfaces. The locking sleeve also includes a collet nut that is threadably engaged to the collet for locking an elongated pin that is received in the elongated pin receiving bore.

The screw threads on the exterior surfaces of the collet arms are interrupted with a band of thread-free zone and the collet nut is provided with one or more detents protruding into the band of thread-free zone and providing a mechanical interference that prevents the collet nut from being removed from the threaded engagement with the collet.

According to another aspect, a locking sleeve for lockably receiving an elongated pin is also disclosed. The locking sleeve comprises an elongated shaft having an elongated pin receiving bore extending therethrough, a collet provided at one end of the elongated shaft, where the collet comprises a plurality of collet arms provided with screw threads integrally formed on their exterior surfaces, and a collet nut that is threadably engaged to the collet for locking an elongated pin that is received in the elongated pin receiving bore.

BRIEF DESCRIPTION OF THE DRAWINGS

The features shown in the above referenced drawings are illustrated schematically and are not intended to be drawn to scale nor are they intended to be shown in precise positional relationship. Like reference numbers indicate like elements.

DETAILED DESCRIPTION

Figure 1:
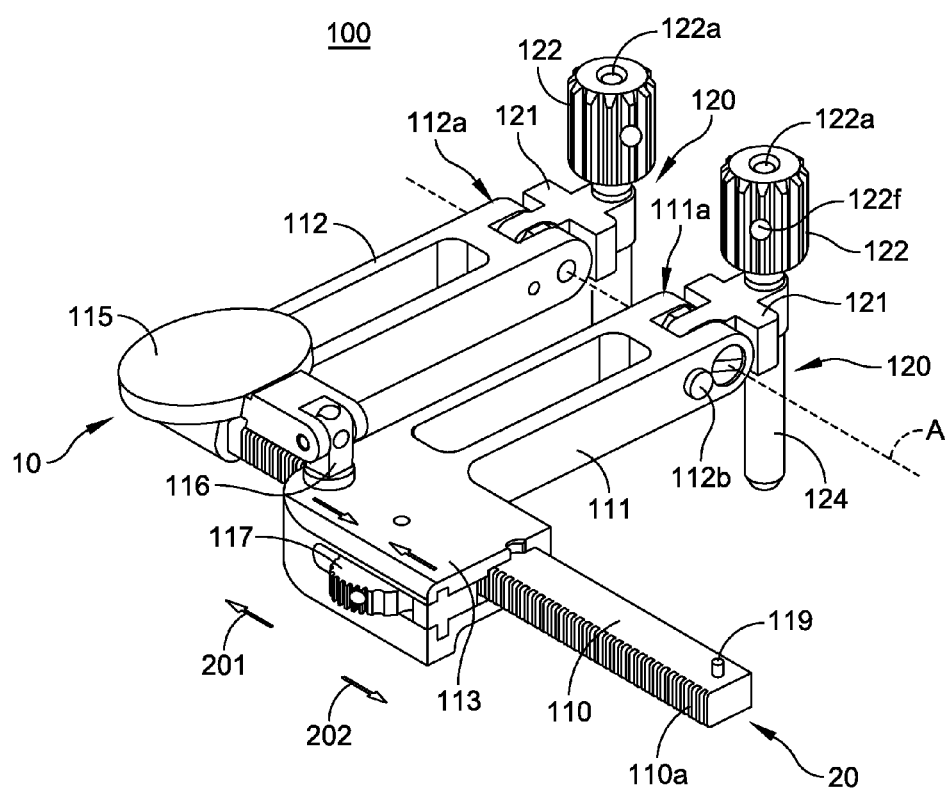
FIG. 1 is an orthographic view of an orthopedic device according to an aspect of the present disclosure.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 2:
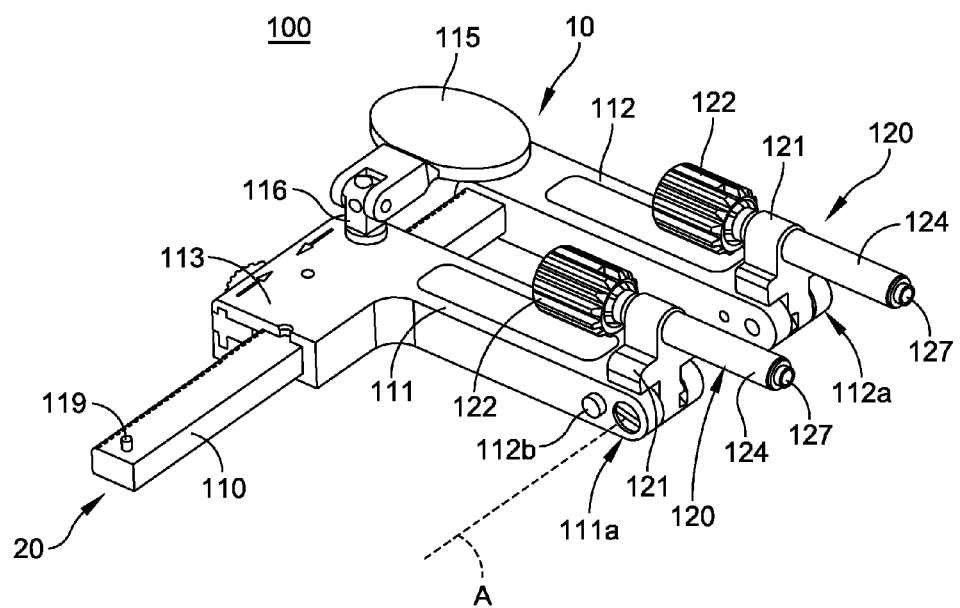
FIG. 2 is another orthographic view of the orthopedic device of FIG. 1.

FIGS. 1-2 show an orthopedic device 100 that can be used for compression or distraction of bone parts according to an aspect of the present disclosure. The orthopedic device 100 comprises an elongated body 110 having first end 10 and a second end 20. A first arm member 112 extends away from the first end 10 in a direction transverse to the elongated body 110 and terminates at an outer end 112a. The first arm member 112 can be integrally formed with the body 110 or otherwise attached to the body 110. A second arm member 111 transversely extends away from the elongated body 110 and terminates at an outer end 111a. The second arm member 111 is configured with a base portion 113 that is configured and adapted to movably engage the elongated body 110 allowing the second arm member 111 to be longitudinally movable along the elongated body.

According to one embodiment, the elongated body 110 is provided with ratchet teeth 110a along its length for engaging with the base portion 113. The base portion 113 is configured with ratcheting mechanisms that can selectably operate in compression or distraction mode. For example, the base portion 113 can be configured with a mode selector switch 117 that can be used to switch between the compression mode and the distraction mode.

The ratcheting mechanism is configured so that the selector switch 117 not only changes the direction of the base portion's movement but also changes the locking direction of the device. This allows the desired compression or distraction to be maintained once it is reached. In the compression mode, the second arm member 111 is locked from moving in the distraction direction 202 and can only move in the compression direction 201. Conversely, in the distraction mode, the second arm member 111 is locked from moving in the compression direction 201 and can only move in the distraction direction 202.

The base portion 113 also can be configured to have a neutral position for the selector switch 117 which will allow the second arm member 111 to freely move along the elongated body 110. The second arm member 111 is moved by turning a turning key handle 115 which is connected to a shaft 116 that actuates the internal mechanism of the base portion 113. The internal structure of the base portion 113, although not shown, is configured with a ratcheting mechanism utilizing a rack and pinion type gear arrangement or other suitable mechanisms known to one skilled in the art.

The elongated body 110 is provided with an appropriate mechanism for stopping the base portion 113 from sliding off the second end 20 of the elongated body 110. For example, in the embodiment shown in FIG. 1, a stop pin 119 provided near the second end 20 of the elongated body serves that function.

The second arm member 111 extends from the elongated body 110 in the same direction as the first arm member 112. The orthopedic device 100 also includes a locking sleeve 120 hingeably connected to the outer end 112a, 111a of each of the first and second arm members 112, 111 by a hinge joint 121, wherein each locking sleeve 120 is configured for lockably receiving an elongated pin (not shown).

The locking sleeve 120 comprises an elongated shaft 124 having an elongated pin receiving bore 127 extending therethrough. Each of the hinge joints 121 hingeably connects one locking sleeve 120 to the outer end of one of the arm members 112, 111. The hinge axes of the hinge joints 121 are coaxially aligned and represented in FIG. 1 by a hinge axis A.

According to an embodiment, the hinge joints 121 can be configured and adapted to be normally locked in a position and prevented from pivoting about the hinge axis A by a spring-loaded locking pin 112b. When the spring-loaded locking pin 112b is pressed, the hinge joint 121 is unlocked and free to pivot about the hinge axis A.

Each of the locking sleeves 120 is connected to the hinge joint 121 so that the elongated shaft 124 and thus the elongated pin receiving bore 127 is oriented transverse to the hinge axis A. The transverse orientation refers to the fact that the elongated shaft 124 and the elongated pin receiving bore 127 are at right angle to the hinge axis A.

According to an embodiment, the locking sleeve 120 further comprises a threaded collet 220 provided at one end of the elongated shaft 124 and a collet nut 122 that is threadably engaged to the threaded collet 220 for locking an elongated pin that is received in the elongated pin receiving bore 127. The threaded collet 220 comprises a plurality of collet arms 221 defining one end of the elongated pin receiving bore 127. The collet arms 221 are provided with screw threads 227 integrally formed on their exterior surfaces whereby said collet nut 122 threadably engages the collets for locking the elongated pin received in the elongated pin receiving bore 127. The integration of the screw threads 227 into the collet arms 221 allow for a low profile, compact design of the collet 220. The collet arms 221 are defined by a plurality of slots 222.

Figure 3:
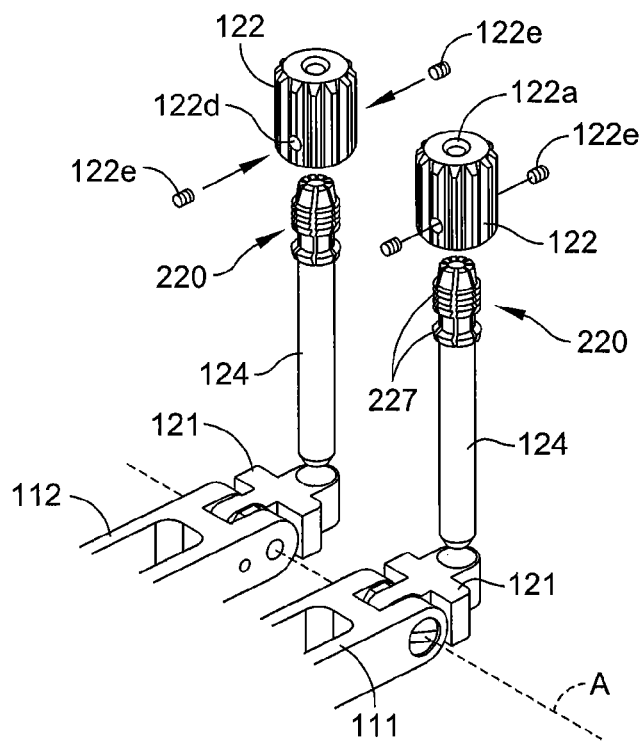
FIG. 3 is an exploded orthographic view of locking sleeves according to an aspect of the present disclosure.
Figure 4:
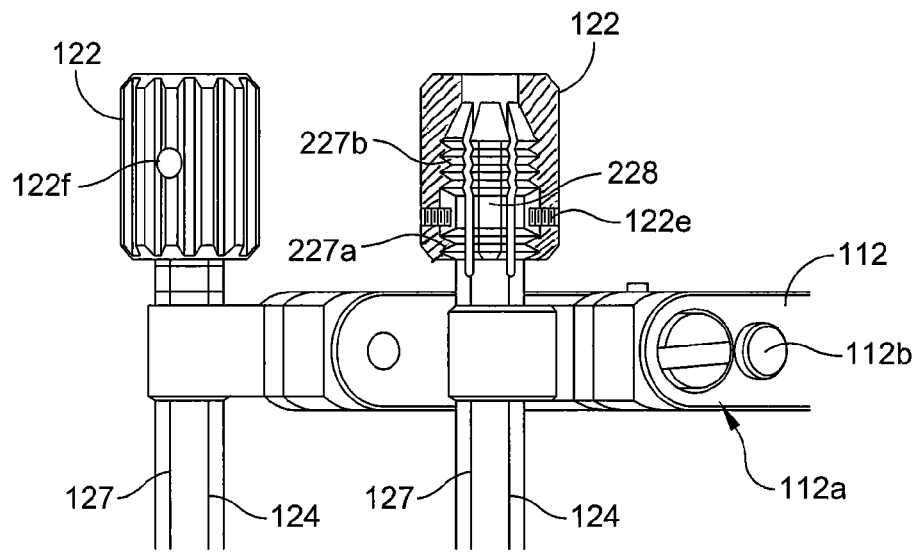
FIG. 4 is an elevation view of the locking sleeves with the collet nut on one of the locking sleeves cross-sectioned.
Figure 5:
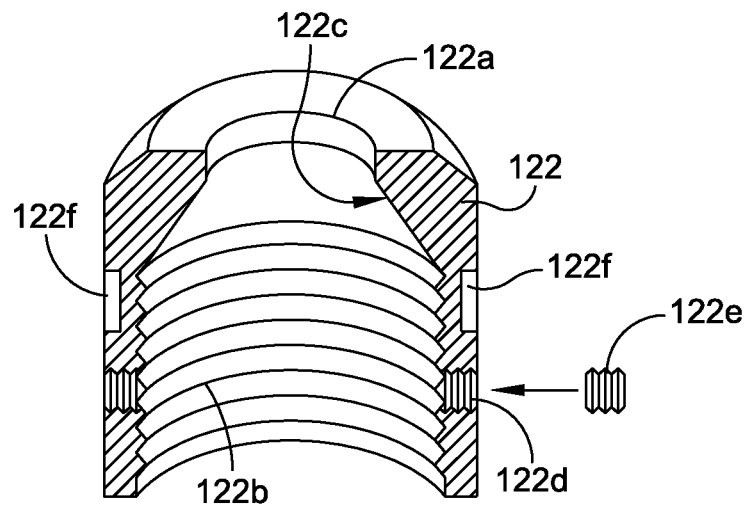
FIG. 5 is an exploded orthographic view showing the threaded collet end of a locking sleeve and a collet nut where the collet nut is shown in cross-section.
Figure 5:
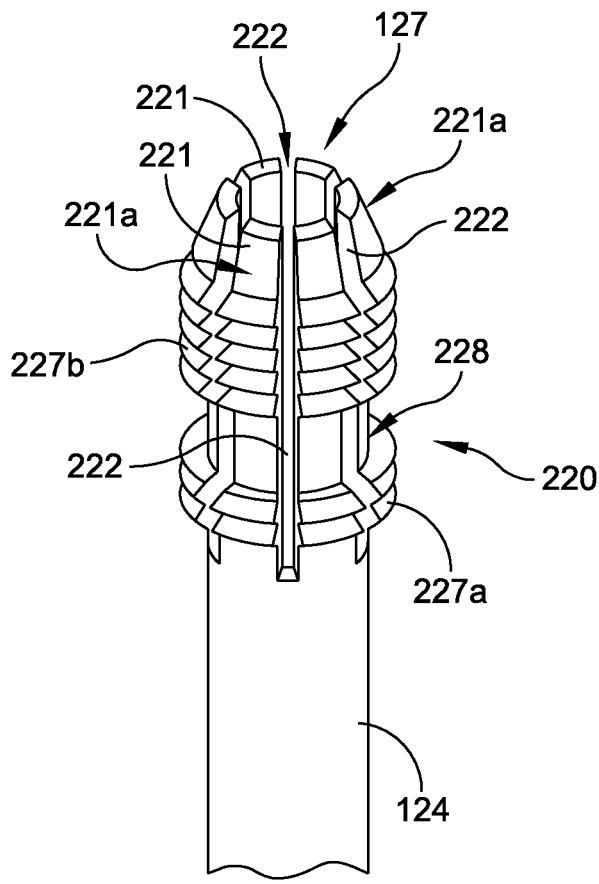

FIGS. 3-5 show detailed structures of the threaded collet 220 and the collet nut 122. As shown in the longitudinal cross-section view of the collet nut 122 in FIG. 5, the collet nut 122 is open at one end for receiving the threaded collet 220 and has an interior surface provided with screw threads 122b for threadably engaging the screw threads 227 of the collet 220. At the end opposite from the threaded collet receiving end, a through hole 122a is provided for the elongated pin received in the elongated pin receiving bore 127. The interior surface of the collet nut 122 is configured with a conical surface 122c. When the collet nut 122 is fully threaded onto the threaded collet 220, the conical surface 122c contacts the collet arms 221 and presses against the chamfered surfaces 221a of the collet arms 221 and pushes the collet arms 221 radially inwards. When an elongated pin is received in the elongated pin receiving bore 127, the threading action of the collet nut 122 causes the collet arms 221 to move radially inward and clamp onto the elongated pin and lock the elongated pin in place.

According to an aspect of the present disclosure, the screw threads 227 on the exterior surfaces of the collet arms 221 are interrupted with a band of thread-free zone 228 dividing the screw threads 227 into a lower portion 227a and an upper portion 227b as shown in FIGS. 4 and 5. The collet nut 122 is provided with one or more detents 122e protruding into the band of thread-free zone 228 and thus providing a mechanical interference with the upper portion 227b of the screw threads that prevents the collet nut 122 from being removed from the threaded engagement with the collet 220. If one tries to remove the collet nut 122, the one or more detents 122e and the upper portion 227b of the screw threads would interfere with each other and prevent the collet nut 122 from being removed.

In one embodiment, the one or more detents 122e are set screws and one or more set screw receiving holes 122d are provided on the side wall of the collet nut 122. The set screw receiving holes 122d are threaded so that a set screw detents 122e can be threaded therein. During assembly of the locking sleeve 120, the collet nut 122 is threaded onto the collet 220 until the set screw receiving holes 122d align with the thread-free zone 228. Then the set screw detents 122e are threaded into the receiving holes 122d until the detents 122e protrude into the thread-free zone 228. In FIG. 4, the sectioned view of one of the collet nut 122 shows this arrangement. The detents 122e can be provided in many other forms than set screws. For example, the detents 122e can be dowel pins of appropriate length that are either press fit, welded or secured in any suitable manner into receiving holes 122d in the collet nut 122.

Generally, it is envisioned that the user can lock an elongated pin received in the elongated receiving bore 127 by tightening the collet nut 122 by hand. According to another aspect of the present disclosure, however, the collet nut 122 can be configured and adapted to accommodate a driver tool for assisting the user in turning and tightening the collet nut.

Figure 6:
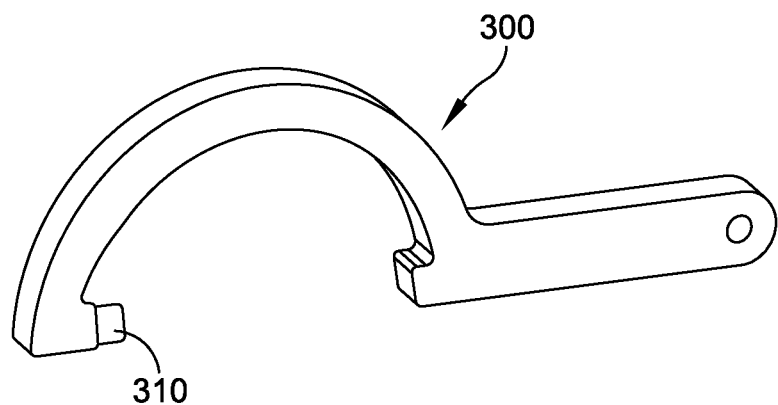
FIG. 6 shows an example of a pin Spanner wrench that can be used to turn the collet nut according to one embodiment.
Figure 7:
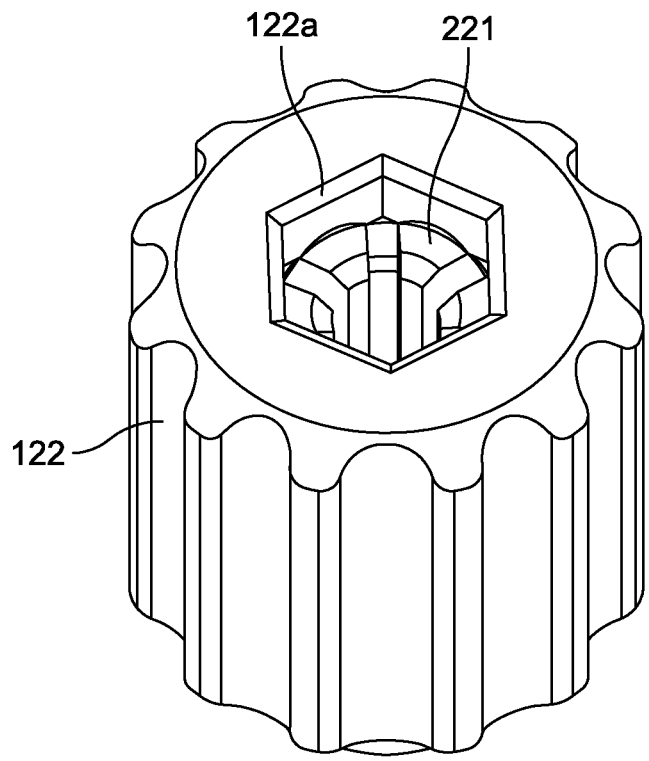
FIG. 7 shows a detailed view of a collet nut according to another embodiment.

In one example, the driver tool can be a pin spanner wrench 300 shown in FIG. 6 and the collet nut is provided with one or more holes or recesses 122f (see FIGS. 1, 4 and 5) along the outer surface of the collet nut for engaging the pin 310 of the driver tool. FIG. 7 shows another embodiment of the collet nut 122 that is configured to be tightened using a cannulated driver tool (not shown) for locking/tightening the collet nut 122. The hollow tubular opening of the cannulated driver tool would accommodate the elongated pin that is positioned in the elongated pin receiving bore 127 of the locking sleeve 120. The through hole 122a of the collet nut can be configured in any variety of shapes as long as it is large enough to allow the elongated pin to pass through it. In this embodiment, the through hole 122a would be provided in a shape that matches the particular driving feature of the driver. For example, if the driver is a hex, square, or star driver, the through hole 122a would be appropriately shaped to engage the driving feature of the driver. In the example shown in FIG. 7, the through hole 122a has a hexagon shape for accommodating a hex tip driver.

As described, the orthopedic device 100 of the present disclosure is a universal device that can be used for compression or distraction of bone parts that are secured to the first and second arm members 112, 111 by elongated pins, such as K-wires, locked into the elongated pin receiving bores 127 of the locking sleeves 120. Referring to FIG. 1, after the bone parts are secured, the movable second arm member 111 can be moved in compression direction 201 or distraction direction 202 by turning the turning key handle 115.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention. The scope of the invention disclosed herein is to be limited only by the following claims.

What is claimed is:

1. An orthopedic device comprising:
an elongated body having first and second ends;
a first arm member attached to and extending away from said first end and terminating at an outer end;
a second arm member extending from said elongated body and having a base portion and an outer end, wherein the base portion is configured and adapted to engage the elongated body and allow the second arm member to be longitudinally movable along said elongated body, said second arm member extending from the elongated body in the same direction as the first arm member; and
a locking sleeve hingeably connected to the outer end of each of the first and second arm members by a hinge joint, wherein said locking sleeve comprises an elongated shaft having an elongated pin receiving bore extending therethrough and a collet provided at one end of the elongated shaft, said collet comprising a plurality of collet arms provided with screw threads integrally formed on their exterior surfaces, and a collet nut that is threadably engaged to the collet for locking an elongated pin that is received in the elongated pin receiving bore.

2. The orthopedic device of claim 1, wherein said screw threads on the exterior surfaces of the collet arms are interrupted with a hand of thread-tree zone and the collet nut is provided with one or more detents protruding into the band of thread-free zone and providing a mechanical interference that prevents the collet urn from being removed from the threaded engagement with the collet.

3. The orthopedic device of claim 2, wherein said one or more detents are set screws that are threaded into the collet nut.

4. The orthopedic device of claim 1, wherein each of said hinge joints having a hinge axis and said hinge axes are in axial alignment.

5. The orthopedic device of claim 4, further wherein each of the locking, sleeves is connected to the hinge joint so that the elongated pin receiving bore is oriented transverse to the hinge axes.

6. The orthopedic device of claim 1, wherein said collet nut is configured and adapted for accommodating a driver tool for turning the collet nut.

7. The orthopedic device of claim 6, wherein said collet nut is provided with one or more recesses on its outer surface for accommodating a pin spanner wrench type driver tool.

8. The orthopedic device of claim 6, wherein said collet nut is provided with a through hole for accommodating the elongated pin that is received in the elongated pin receiving bore and said through hole has an outline that is shaped to match the driver tool's driving feature.

9. A locking sleeve for lockably receiving an elongated pin, said sleeve comprising:
an elongated shaft having an elongated pin receiving bore extending therethrough;
a collet provided at one end of the elongated shaft, said collet comprising a plurality of collet arms provided with screw threads integrally formed on their exterior surfaces, wherein the collet arms are integrally formed at the end of the elongated shaft; and
a collet nut that is threadably engaged to the collet for locking an elongated pin that is received in the elongated pin receiving bore.

10. The locking sleeve of claim 9, wherein said screw threads on the exterior surfaces of the collet arms are interrupted with a band of thread-free zone and the collet nut is provided with one or more detents protruding into the hand of thread-free zone and providing a mechanical interference that prevents the collet nut from being removed from the threaded engagement with the collet.

11. The locking sleeve, of claim 10, wherein said one or more detents are set screws that are threaded into the collet nut.

12. The locking sleeve of claim 9, wherein said collet nut is configured and adapted for accommodating a driver tool for turning the collet nut.

13. The locking sleeve of claim 12, wherein said collet nut is provided with one or more recesses on its outer surface for accommodating a pin spanner wrench type driver tool.

14. The locking sleeve of claim 12, wherein said collet nut is provided with a through hole for accommodating the elongated pin that is received in the elongated pin receiving bore and said through hole has an outline that is shaped to match the driver tool's driving feature.

15. The orthopedic device of claim 1, wherein the collet arms are integrally formed at the end of the elongated shaft.

16. A device, comprising:
a locking sleeve including
an elongate shaft defining a pin receiving bore therethrough, the elongate shaft defining a plurality of slots extending longitudinally from a first end of the elongate shaft to a first position along a length of the elongate shaft to provide a plurality of collet arms, the plurality of collet arms including a first set of integrally formed screw threads on their exterior surfaces;
a collet nut configured to engage the first set of integrally formed screw threads to inwardly deflect the plurality of collet arms,
wherein the first set of integrally formed threads are disposed adjacent to the first end and at a distance from the first position.

17. The device of claim 16, wherein the a second set of integrally formed screw threads along the length of the plurality of collet arms at a distance from the first set of integrally formed threads.

18. The device of claim 16, wherein the collet nut includes an inner surface that is at least partially conical and is configured to engage a chamfered surface of each of the plurality of collet arms to facilitate compression of the plurality of collet arms.

19. The device of claim 16, further comprising;
an elongated body having first and second ends;
a first arm member attached to and extending away from said first end of the elongated body and terminating at an outer end;

a second arm member extending from said elongated body of the elongated body and having a base portion and an outer end, wherein the base portion is configured and adapted to engage the elongated body and allow the second arm member to be longitudinally movable along said elongated body, said second arm member extending from the elongated body in the same direction as the first arm member.

* * * * *